United States Patent
Foley

(10) Patent No.: US 10,548,821 B2
(45) Date of Patent: Feb. 4, 2020

(54) TOPICAL SKIN FORMULATION

(75) Inventor: Bob Foley, Coppell, TX (US)

(73) Assignee: Mary Kay Inc., Addison, TX (US)

( * ) Notice: Subject to any disclaimer, the term of this patent is extended or adjusted under 35 U.S.C. 154(b) by 0 days.

(21) Appl. No.: 13/698,016

(22) PCT Filed: May 17, 2011

(86) PCT No.: PCT/US2011/036818
§ 371 (c)(1),
(2), (4) Date: Jan. 3, 2013

(87) PCT Pub. No.: WO2011/146491
PCT Pub. Date: Nov. 24, 2011

(65) Prior Publication Data
US 2013/0118517 A1    May 16, 2013

Related U.S. Application Data

(60) Provisional application No. 61/345,440, filed on May 17, 2010.

(51) Int. Cl.
*A61K 8/04* (2006.01)
*A61Q 1/00* (2006.01)
*A61Q 17/04* (2006.01)

(52) U.S. Cl.
CPC ............... *A61K 8/042* (2013.01); *A61Q 1/00* (2013.01); *A61Q 17/04* (2013.01)

(58) Field of Classification Search
None
See application file for complete search history.

(56) References Cited

U.S. PATENT DOCUMENTS

| | | | |
|---|---|---|---|
| 2,798,053 A | 7/1957 | Brown | 521/38 |
| 3,755,560 A | 8/1973 | Dicker et al. | 514/772.6 |
| 4,421,769 A | 12/1983 | Dixon et al. | 514/772 |
| 4,509,949 A | 4/1985 | Huang et al. | 8/558 |
| 4,599,379 A | 7/1986 | Flesher et al. | 524/801 |
| 4,628,078 A | 12/1986 | Glover et al. | 526/303.1 |
| 4,835,206 A | 5/1989 | Farrar et al. | 524/457 |
| 4,849,484 A | 7/1989 | Heard | 525/221 |
| 5,011,681 A | 4/1991 | Ciotti et al. | 510/136 |
| 5,087,445 A | 2/1992 | Haffey et al. | 424/59 |
| 5,100,660 A | 3/1992 | Hawe et al. | 424/78.35 |
| 5,576,354 A | 11/1996 | Deflandre et al. | 514/685 |
| 5,587,150 A | 12/1996 | Deflandre et al. | 424/59 |
| 5,667,765 A | 9/1997 | Hansenne et al. | 424/59 |
| 5,908,631 A * | 6/1999 | Arnaud | A61K 8/37 424/401 |
| 6,060,546 A | 5/2000 | Powell et al. | 524/267 |
| 6,200,964 B1 * | 3/2001 | Singleton et al. | 514/159 |
| 6,387,405 B1 * | 5/2002 | Shah et al. | 424/486 |
| 6,916,464 B2 * | 7/2005 | Hansenne et al. | 424/59 |
| 2004/0126336 A1 | 7/2004 | Hansenne et al. | 424/59 |
| 2008/0206371 A1 | 8/2008 | Fontaine et al. | 424/744 |
| 2010/0092408 A1 * | 4/2010 | Breyfogle et al. | 424/59 |

FOREIGN PATENT DOCUMENTS

| | | | | |
|---|---|---|---|---|
| EP | 2179721 A1 * | 4/2010 | | A61K 8/894 |
| JP | 2003-063927 | 3/2003 | | |

OTHER PUBLICATIONS

CAS registry entry for "octisalate" copyright 2013.*
Personal Care's "Formulating for a consumer-perceivable difference," published Nov. 2009; http://www.personalcaremagazine.com/Print.aspx?Story=5952.*
Google Patent translation EP 2179721, printed 2019.*
Diffey, "A method for broad-spectrum classification of sunscreens", Int. J. Cosmet. Sci. 1994, 16:47-52.
International Cosmetic Ingredient Dictionary and Handbook, 12$^{th}$ Edition (2008), vol. 3, pp. 3271-3273, "Solvents".
"Lucidity Anhydrous Sunscreen Gel", Dow Corning; May 5, 2009. URL: http://www.dowcorning.de/de_DE/content/publishedlit/FORMUL_01312.pdf.
"Suncare compositions with new cosmetic raw materials." IP.com Journal, IP.Com Inc., West Henrietta, NY, US. Mar. 2, 2010.
"Dow Corning® EL-8050 ID Silicone Organic Elastomer Blend", Dow Corning, Mar. 5, 2013. URL: http://www3.dowcorning.com/DataFiles/090007b281c9d509.pdf.
"Crodamol GTCC", Croda International plc, 2014. URL: http://www.croda.com/home.aspx?view=dtl&d=content&s=157&r=273&p=1859&prodID=134.
International Preliminary Report on Patentabilioty issued in PCT/US2011/036818, dated May 22, 2014.
Office Action issued in Chinese Application No. 201180024925.4, dated Aug. 15, 2014.
"Airbrush FX Face Primer SPF 20", Mintel GNPD, 2009.
International Search Report and Written Opinion issued in Application No. PCT/US2011/036818, dated May 8, 2014.

* cited by examiner

*Primary Examiner* — Ileana Popa
*Assistant Examiner* — Alissa Prosser
(74) *Attorney, Agent, or Firm* — Norton Rose Fulbright US LLP

(57) ABSTRACT

Disclosed is a gel, and corresponding methods for its use, having an SPF of at least 15 comprising at least about 50% by weight of a volatile hydrocarbon, a film former, a solvent comprising an ester group, a combination of ultraviolet A (UVA) and ultraviolet B (UVB) sunscreen agents, wherein the UVA sunscreen agent comprises 4-tert-butyl-4'-methoxydibenzoylmethane, wherein the PFA of the gel is at least about 5 or at least about 8, and wherein the gel is capable of drying within two minutes after topical application to skin.

2 Claims, No Drawings

TOPICAL SKIN FORMULATION

CROSS REFERENCE TO RELATED APPLICATIONS

This application is a national phase application under 35 U.S.C. § 371 of International Application No. PCT/US2011/036818, filed May 17, 2011, which claims the benefit of U.S. Provisional Application No. 61/345,440, filed May 17, 2010. The contents of the aforementioned applications are incorporated by reference.

BACKGROUND OF THE INVENTION

A. Field of the Invention

The present invention relates generally to topical skin care compositions. In particular aspects, the compositions can be used as a primer for subsequent application of additional cosmetic products (e.g., foundations).

B. Description of Related Art

Foundation primers create a barrier between a user's skin and a cosmetic product (e.g., foundations). Primers can provide a smooth or even surface for subsequent application of a foundation. This barrier allows for a more even application and increased durability of the foundation via reducing the contact between the foundation and sebum or skin perspiration.

A majority of foundation primers have an opaque appearance. This can help shield the skin from ultra violet radiation. However, the opacity can affect the coloring of the foundation that is subsequently applied.

Although some transparent and translucent primers exist that claim to have ultra violet protection properties, such formulations tend to have relatively high amounts of non-volatile solvents to ensure photostability of the sunscreen agents. The problem with this is that such solvents can create unpleasant tactile properties (e.g., heavy and greasy feel) and can result in a primer that takes prolonged periods of time to dry once applied to skin.

SUMMARY OF THE INVENTION

The inventor has discovered a gel-based composition that has pleasant tactile properties, can dry within about two minutes, 1 minute, or 30 seconds after topical application to skin, and can offer both ultraviolet A(UVA) and ultraviolet B (UVB) protection to skin. The gel can be translucent or transparent. In certain aspects, the color can be clear (i.e., colorless) or white.

In one embodiment, there is disclosed a gel having an SPF of at least 15 comprising at least about 50% by weight of a volatile hydrocarbon, a film former, a solvent comprising an ester group, and a combination of UVA and UVB chemical sunscreen agents, wherein the UVA sunscreen agent comprises 4-tert-butyl-4'-methoxydibenzoylmethane, wherein the gel is capable of drying or formulated so that it dries within 5, 4, 3, 2, or 1 minute or 30 seconds after topical application to the skin. The gel can have a protection grade for UVA ("PFA") of at least about 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, or more. In particular aspects, the PFA of the gel is between 5 and 10, 8 and 10, or 8 and 9. In another aspect, the PFA can be greater than 5, 6, 7, 8, 9, or 10, or more. In one aspect, the PFA of the gel can be at least ⅓ or ½ or more of the value of the SPF of the gel. In certain aspects, the ratio of SPF to PFA values can range from 4:1 to 1:1, 3:1, to 1:1, 2:1 to 1:1, or 1.5:1 to 1:1. The skin can be facial skin or body skin (e.g., neck, shoulders, back, chest, arms, hands, abdomen, buttocks, legs, feet, etc.). In particular embodiments, the volatile hydrocarbon is isododecane. In one aspect, the solvent comprising an ester group can be selected from the group consisting of C12-15 alkyl benzoate and neopentyl glycol diheptanoate and a combination of both. The film former can be selected from the group consisting of polysilicone-11, VP hexedecene copolymer, and polyester-7 and any combination thereof or all of these polymers. In one aspect, the UVA protection of the gel is at least about ½ of the SPF of the gel. The gel can be dermatologically acceptable for topical application to human skin. After the gel is applied to skin, a cosmetic product can be applied onto the gel. The UVA sunscreen agent can be partially, substantially, or completely solubilized in the gel. It can be solubilized in the gel and can remain solubilized when the gel is stored at 5° C. for four weeks. The gel can be photostable when stored at 5° C. for four weeks. In certain aspects, the gel can be translucent or transparent prior to application to skin. It can be translucent or transparent after application to skin. The gel can have a viscosity ranging from 80,000 to 160,000 cps (or any range or integer therein such as 90,000, 100,000, 110,000, 120,000, 130,000, 140,000, 150,000, etc.). In one embodiment, the gel includes between 55% to 65% by weight of the volatile hydrocarbon. In another aspect, the gel can include 5% to 10% by weight of the film former. In certain embodiments, the gel can include 2% to 5% by weight of the solvent. The gel can be cyclomethicone-free, oil-free, and/or free of physical sunscreen agents (e.g., titanium dioxide, zinc oxide, etc.). In one instance, the critical wavelength of the protection of that the gel offers from UV radiation is approximately 370 nm. In certain aspects, at least about 90% of the UV radiation protection offered by the gel falls within about 290 nm-370 nm in wavelength. In certain aspects, the gel can further comprise silica (which can be helpful for absorbing ingredients such as sebum), skin conditioners (which can be helpful to moisturize skin), and/or emollients (which can be helpful to retain skin moisture). Non-limiting examples of skin conditioners include tribehenin. Non-limiting examples of emollients include dipropylene glycol debenzoate and PPG-15 stearyl ether benzoate. The composition can also include a gelling agent (a non-limiting example of which can be dimethicone/bis-isobutyl PPG-20 crosspolymer). In particular embodiments, the combination of sunscreen agents includes 4-tert-butyl-4'-methoxydibenzoylmethane, 2-ethylhexyl 2-cyano-3,3-diphenyl-2-propenoate, 3,3,5-Trimethylcyclohexyl 2-hydroxybenzoate, and 2-ethylhexyl 2-hydroxybenzoate. In certain aspects, the SPF of the gel can be 20, 25, 30, 35, 40, 45, 50, 55, 60, or more, or any integer or derivative therein. In other aspects, the SPF can be less than 15, 10, 5, 2, etc.).

In one embodiment, there is disclosed a gel having an SPF of at least 15 comprising 55% to 65% by weight of a volatile hydrocarbon, 5% to 10% by weight of a film former, 2% to 5% by weight of a solvent comprising an ester group, and a combination of ultraviolet A (UVA) and ultraviolet B (UVB) sunscreen agents, wherein the UVA sunscreen agent comprises 4-tert-butyl-4'-methoxydibenzoylmethane, wherein the UVA protection of the gel is at least ⅓ the value of the SPF of the gel, and wherein the gel is capable of drying or is formulated to dry within 5, 4, 3, 2, or 1 minute or 30 seconds after topical application to the skin. The skin can be facial skin or body skin (e.g., neck, shoulders, back, chest, arms, hands, abdomen, buttocks, legs, feet, etc.). The volatile hydrocarbon can be isododecane, the film former can be a combination of polysilicone-11, VP/hexadecene copolymer, and polyester 7, the solvent can be a combination of C12-15 alkyl benzoate and neopentyl glycol diheptanoate, and the combination of (UVA) and (UVB) ingredients can be 4-tert-butyl-4'-methoxydibenzoylmethane, 2-ethylhexyl 2-cyano-3,3-diphenyl-2-propenoate, 3,3,5-Trimethylcyclohexyl 2-hydroxybenzoate, and 2-ethylhexyl 2-hydroxybenzoate.

In another aspect of the present invention there is disclosed a translucent gel comprising, consisting essentially of, or consisting of: at least 50% w/w isododecane; homosalate; dimethicone/bis-isobutyl PPG-20 crosspolymer; octisalate; polysilicone-11; VP/hexadecene copolymer; octocrylene; avobenzone; silica; C12-15 alkyl benzoate; polyester-7; tribehenin; neopentyl glycol diheptanoate; dipropylene glycol dibenzoate; and PPG-15 stearyl ether benzoate. In particular aspects, the gel comprises 58.7% w/w isododecane; 9% w/w homosalate; 5.5 w/w % dimethicone/bis-isobutyle PPG-20 crosspolymer; 5% w/w octisalate; 3.72% polysilicone-11; 3.5% w/w VP/hexadecene copolymer; 3% w/w octocrylene; 2.5% w/w avobenzone; 2.5% w/w silica; 2.1% w/w C12-15 alkyl benzoate; 1.5% w/w polyester-7; 1% w/w tribehenin; 1% w/w neopentyl glycol diheptanoate; 0.75% w/w dipropylene glycol dibenzoate; and 0.15% w/w PPG-15 stearyl ether benzoate.

Also disclosed is a method of applying a cosmetic composition to skin comprising applying any one of the gels disclosed throughout this specification to skin, and subsequently applying a cosmetic composition onto the gel. The cosmetic composition can be applied after the gel has dried on the skin. The gel can dry on the skin within 5, 4, 3, 2, or 1 minute or within 30 seconds after topical application to the skin. The cosmetic composition can be a foundation product. The skin can be facial skin or body skin (e.g., neck, shoulders, back, chest, arms, hands, abdomen, buttocks, legs, feet, etc.).

In another embodiment there is disclosed a method for increasing the duration that a cosmetic composition can be worn on skin comprising applying any one of the gels disclosed throughout this specification to skin, and subsequently applying a cosmetic composition onto the gel. The cosmetic composition can be applied after the gel has dried on the skin. The gel can dry on the skin within 5, 4, 3, 2, or 1 minute or within 30 seconds after topical application to the skin. The cosmetic composition can be a foundation product. The skin can be facial skin or body skin (e.g., neck, shoulders, back, chest, arms, hands, abdomen, buttocks, legs, feet, etc.).

In yet another aspect of the present invention there is disclosed a method for protecting a cosmetic composition from degrading on skin comprising applying any one of the gels disclosed throughout the specification to skin and subsequently applying the cosmetic composition onto the gel. The cosmetic composition can be applied after the gel has dried on the skin. The gel can dry on the skin within 5, 4, 3, 2, or 1 minute or 30 seconds after topical application to the skin. The cosmetic composition can be a foundation product. The skin can be facial skin or body skin (e.g., neck, shoulders, back, chest, arms, hands, abdomen, buttocks, legs, feet, etc.).

A further embodiment of the present invention concerns a method for evening out skin texture (e.g., by filing in or smoothing out fine lines or wrinkles, pits, nodules, cracks, creases, pores, etc.) comprising topically applying any one of the gels of the present invention to fine lines or wrinkles, pits, nodules, cracks, creases, pores, etc. The gel can dry on the skin within 5, 4, 3, 2, or 1 minute or 30 seconds after topical application to the skin.

Also disclosed is a method for evening out a person's skin tone or texture or improving a person's skin complexion comprising topically applying any one of the gels of the present invention to blotchy skin, red skin, melasmic skin, dark spots, aged spots, brown spots, or otherwise disclosed skin. The gel can dry on the skin within 5, 4, 3, 2, or 1 minute or 30 seconds after topical application to the skin.

Kits that include the gels of the present invention are also contemplated. In certain embodiments, the composition is comprised in a container. The container can be a bottle, dispenser, or package. The container can dispense a predetermined amount of the composition. In certain aspects, the compositions is dispensed in a spray, dollop, or liquid. The container can include indicia on its surface. The indicia can be a word, an abbreviation, a picture, or a symbol.

It is contemplated that any embodiment discussed in this specification can be implemented with respect to any method or composition of the invention, and vice versa. Furthermore, compositions of the invention can be used to achieve methods of the invention.

In one embodiment, the topical skin compositions of the current invention are pharmaceutically elegant. "Pharmaceutically elegant" describes a composition that has particular tactile properties which feel pleasant on the skin (e.g., compositions that are not too watery or greasy, compositions that have a silky texture, compositions that are non-tacky or sticky, etc.). Pharmaceutically elegant can also relate to the creaminess or lubricity properties of the composition or to the moisture retaining properties of the composition.

The terms "dry," "dries," "drying" or any variation thereof means that the compositions described throughout the specification are in a un-flowable state. By way of example, a composition of the present invention that dries within two minutes or 1 minute or 30 seconds after topical application to skin is in an un-flowable state.

"Transparent" means that the composition permits light to pass through it so that objects situated beyond or behind the composition are clearly or distinctly visible.

"Translucent" or "semi-transparent" means that the composition permits light to pass through it but diffuses the light so that objects situated beyond or behind the composition are visible but not clearly or distinctly visible.

"Keratinous tissue" includes keratin-containing layers disposed as the outermost protective covering of mammals and includes, but is not limited to, skin, hair and nails.

"Topical application" means to apply or spread a composition onto the surface of keratinous tissue. "Topical skin composition" includes compositions suitable for topical application on keratinous tissue. Such compositions are typically dermatologically-acceptable in that they do not have undue toxicity, incompatibility, instability, allergic response, and the like, when applied to skin. Topical skin care compositions of the present invention can have a selected viscosity to avoid significant dripping or pooling after application to skin.

The term "about" or "approximately" are defined as being close to as understood by one of ordinary skill in the art, and in one non-limiting embodiment the terms are defined to be within 10%, preferably within 5%, more preferably within 1%, and most preferably within 0.5%.

The terms "inhibiting" or "reducing" or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

The use of the word "a" or "an" when used in conjunction with the term "comprising" in the claims and/or the specification may mean "one," but it is also consistent with the meaning of "one or more," "at least one," and "one or more than one."

The use of the term "or" in the claims is used to mean "and/or" unless explicitly indicated to refer to alternatives only or the alternatives are mutually exclusive, although the disclosure supports a definition that refers to only alternatives and "and/or."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The compositions of the present invention can comprise, consist essentially of, or consist of the claimed ingredients. In one aspect, compositions consisting essentially of the claimed ingredients excludes ingredients that would materially affect the photostability of the UV ingredients and/or would increase the drying time of the composition to greater than two minutes after topical application to skin.

Other objects, features and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

DESCRIPTION OF ILLUSTRATIVE EMBODIMENTS

Although cosmetic compositions currently exist that can be used to "prime" a person's skin for subsequent application of a second cosmetic composition (e.g., foundation), these "primers" either lack sufficient capabilities to protect skin from both UVA and UVB radiation, are opaque in appearance which can negatively affect the color of the second composition being applied onto the primer, have unpleasant tactile properties that leave the skin feeling oily and greasy, or take prolonged periods of time to sufficiently dry on the skin which delays the process of applying the second composition.

It is important to be able to protect skin from both UVA and UVB radiation. Over exposure to UVA radiation can lead to premature skin aging (e.g., increased appearance in fine lines and wrinkles, loss of skin elasticity, loss of skin moisture), symptoms that can take years to show on skin. By comparison, over exposure to UVB radiation, which can cause skin cancer, is commonly associated with sun tanned skin and sunburns. Because the symptoms of overexposure to UVB radiation can manifest within a short period of time (e.g., within minutes to hours of exposure), several sunscreen products protect against UVB radiation with limited protection offered against UVA radiation.

In this regard, a sunscreen product claiming to have a particular Sun Protection Factor ("SPF") number refers to the product's ability to protect the skin from sunburns. For instance, the SPF of a sunscreen is the amount of UV radiation required to cause a sunburn on the skin with the sunscreen on the skin, relative to the amount required to burn the skin without being protected with sunscreen. Applying a sunscreen having an SPF of 10 to skin provides the skin with 10 times the amount of protection from sunburns—i.e., it should take 10 times as long to obtain a sunburn when compared with unprotected skin.

One of the problems associated with SPF values is that this value only accounts for a product's ability to protect the skin against sunburns (which is caused by UVB radiation). An SPF value of a given product is not indicative of whether the product can protect skin from UVA radiation.

In contrast to SPF values, the Protection Grade of UVA ("PFA") value typically refers to a composition's ability to provide protection from UVA radiation. PFA values between 2-4 (also referred to as PA +) indicate that the composition provides limited protection against UVA radiation. PFA values between 4-8 (also referred to as PA ++) indicate that the composition provides moderate protection from UVA radiation. PFA values of 8 or more (also referred to as PA +++) indicate that the composition provides a substantial protection from UVA radiation.

A majority of foundation primer products provide limited to no protection from UV radiation. One of the reasons for this is that additional cosmetic compositions are being applied on top of the primer. Therefore, it is thought that the additional composition can provide the necessary UV radiation protection to skin.

There are sunscreens that provide sufficient protection against both UVA and UVB radiation. A well-known UVA sunscreen agent is avobenzone (4-tert-butyl-4'-methoxydibenzoylmethane), which is highly lipophilic in nature. Due to its lipophilicity, a relatively high amount of non-volatile hydrophobic ingredients are needed to ensure that avobenzone is sufficient solubilzed in a given formulation (high amounts of volatile hydrocarbons can cause insolubility issues with avobenzone). The downside to having high amounts of non-volatile hydrophobic ingredients, however, is that it leads to compositions that have an oily or heavy feel when applied to skin. Further, the compositions take a prolonged period of time to actually dry on the skin (e.g., much longer than two minutes), thus making them inadequate for use as primers.

The inventor has discovered a solution to the aforementioned problems associated with primer based products. This solution takes the form of a transparent or translucent gel-based composition surprisingly having at least 50% by weight of a volatile hydrocarbon. The gel is capable of protecting skin from the harmful effects of both UVA and UVB rays. Because of the high amounts of the volatile hydrocarbon, the gel is also capable of drying within two minutes, one minute, or thirty seconds after topical application to skin, thereby making it sufficient to be used as a cosmetic primer. As shown in the examples, the composition has an SPF of at least about 15 and a PFA of at least about 8, thereby providing effective protection from both UVB and UVA radiation.

These and other non-limiting aspects of the gel-based composition of the present invention are disclosed in the following sections.

A. Volatile Hydrocarbons

Volatile hydrocarbons include hydrocarbons that are liquid at normal pressure and temperature but have a high vapor pressure and therefore evaporate rapidly. Non-limiting examples of volatile hydrocarbons that can be used in the context of the present invention include volatile saturated hydrocarbons (i.e., alkanes), volatile unsaturated hydrocarbons (i.e., hydrocarbons that have one or more double or triple bonds between carbon atoms such as alkenes and alkynes), volatile cycloalkanes, and volatile aromatic hydrocarbons. The International Cosmetic Ingredient Dictionary and Handbook, 12$^{th}$ Edition (2008) ("CTFA Handbook") at volume 3, pages 3271-3273, provide a wide range of volatile hydrocarbons that can be used in the context of the present invention, all of which are incorporated by reference. Non-limiting examples of such hydrocarbons include isododecane, isoeicosane, isohexadecane, and Isooctane.

B. Film Formers

Film formers are materials or compound, which, upon drying, can produce a continuous film on skin. This can increase the durability of a composition while also resulting in reduced moisture loss from skin. The CTFA Handbook at volume 3, pages 3187-3192, provides a wide range of film formers that can be used in the context of the present invention, all of which are incorporated by reference. Non-limiting examples of such film formers include Polysilicone-6, Polysilicone-8, Polysilicone-11, Polysilicone-14, VP/Dimethiconylacrylate/Polycarbamyl/Polyglycol Ester, VP/Dimethylaminoethylmethacrylate Copolymer, VP/Dimethylamino ethylmethacrylate/Polycarbamyl Polyglycol Ester, VP/Eicosene Copolymer, VP/Hexadecene Copolymer, VP/Methacrylamide/Vinyl Imidazole Copolymer, VP/Polycarbamyl Polyglycol Ester, VP/VA Copolymer, Polyester-1, Polyester-2, Polyester-3, Polyester-4, Polyester-5, Polyester-7, Polyester-8, and Polyester-10.

C. Ester Containing Solvents

Esters are covalent compounds formed between acids and alcohols. They can be used to stabilize and solubilze sunscreen agents in the context of the present invention. The CTFA Handbook at volume 3, pages 3079-3088, provides a wide range of ester containing solvents that can be used in the context of the present invention, all of which are incorporated by reference. Non-limiting examples of such solvents include C12-15 Alkyl benzoate, neopentyl glycol diheptanoate, dipropylene glycol dibenzoate, and PPG-15 stearyl ether benzoate.

D. Sunscreen Agents

As noted above, the inventor discovered that sunscreen agents can be incorporated into a gel-based composition having at least about 50% by weight of a volatile hydrocarbon and still remain photo stable after topical application to skin for prolonged periods of time. The following combination of sunscreen agents work well in the context of the present invention: 3,3,5-Trimethylcyclohexyl 2-hydroxybenzoate (also known as homosalate), 2-ethylhexyl 2-hydroxybenzoate (also known as octisalate), 2-ethylhexyl 2-cyano-3,3-diphenyl-2-propenoate (also known as octocrylene), and 1-(4-methoxyphenyl)-3-(4-tert-butylphenyl) propane-1,3-dione (also known as avobenzone, butylmethoxydibenzoylmethane, or 4-tert-butyl-4'-methoxydibenzoylmethane). This combination of ingredients can be used to produce a photo stable gel-based primer having an SPF of at least 15 while also providing the user with protection from UVB and UVA radiation in a ratio of 3:1 (UVB:UVA).

It is contemplated that additional sunscreen agents can be used in the context of the present invention (either as additives or replacements to those mentioned in the above paragraph). Non-limiting examples of such agents include para-aminobenzoic acid (PABA), PABA esters (glyceryl PABA, amyldimethyl PABA and octyldimethyl PABA), butyl PABA, ethyl PABA, ethyl dihydroxypropyl PABA, benzophenones (oxybenzone, sulisobenzone, benzophenone, and benzophenone-1 through 12), cinnamates (octyl methoxycinnamate, isoamyl p-methoxycinnamate, octyl-methoxy cinnamate, cinoxate, diisopropyl methyl cinnamate, DEA-methoxycinnamate, ethyl diisopropylcinnamate, glyceryl octanoate dimethoxycinnamate and ethyl methoxycinnamate), cinnamate esters, salicylates (benzyl salicylate, glycol salicylate, isopropylbenzyl salicylate, etc.), anthranilates, ethyl urocanate, other dibenzoylmethane derivatives, octyl triazone, digalloy trioleate, glyceryl aminobenzoate, lawsone with dihydroxyacetone, ethylhexyl triazone, dioctyl butamido triazone, benzylidene malonate polysiloxane, terephthalylidene dicamphor sulfonic acid, disodium phenyl dibenzimidazole tetrasulfonate, diethylamino hydroxybenzoyl hexyl benzoate, bis diethylamino hydroxybenzoyl benzoate, bis benzoxazoylphenyl ethylhexylimino triazine, drometrizole trisiloxane, methylene bis-benzotriazolyl tetramethylbutylphenol, and bis-ethylhexyloxyphenol methoxyphenyltriazine, 4-methylbenzylidenecamphor, and isopentyl 4-methoxycinnamate.

E. Gelling Agents

The composition of the present invention can be formulated as a transparent gel. Gelling agents such as dimethicone/bis-isobutyl PPG-20 crosspolymer can used to create the gel-based primer. Further, a wide range of gelling agents are commercially available from Dow Corning (Midland, Mich. (USA)). A non-limiting example includes Dow Corning EL-8050 ID, which is a blend of dimethicone/bis-isobutyl PPG-20 crosspolymer and isododecane.

F. Compositions of the Present Invention

1. Combinations and Amounts of Ingredients

It is contemplated that the compositions of the present invention can include any one of the volatile hydrocarbons, film formers, ester-based solvents, sunscreen agents, and gelling agents, or any combination of these ingredients. The compositions can also include additional ingredients described throughout this specification. The concentrations of the volatile hydrocarbons, film formers, ester-based solvents, sunscreen agents, gelling agents, or any additional ingredients can vary. In non-limiting embodiments, for example, the compositions can include in their final form, for example, at least about 0.0001%, 0.0002%, 0.0003%, 0.0004%, 0.0005%, 0.0006%, 0.0007%, 0.0008%, 0.0009%, 0.0010%, 0.0011%, 0.0012%, 0.0013%, 0.0014%, 0.0015%, 0.0016%, 0.0017%, 0.0018%, 0.0019%, 0.0020%, 0.0021%, 0.0022%, 0.0023%, 0.0024%, 0.0025%, 0.0026%, 0.0027%, 0.0028%, 0.0029%, 0.0030%, 0.0031%, 0.0032%, 0.0033%, 0.0034%, 0.0035%, 0.0036%, 0.0037%, 0.0038%, 0.0039%, 0.0040%, 0.0041%, 0.0042%, 0.0043%, 0.0044%, 0.0045%, 0.0046%, 0.0047%, 0.0048%, 0.0049%, 0.0050%, 0.0051%, 0.0052%, 0.0053%, 0.0054%, 0.0055%, 0.0056%, 0.0057%, 0.0058%, 0.0059%, 0.0060%, 0.0061%, 0.0062%, 0.0063%, 0.0064%, 0.0065%, 0.0066%, 0.0067%, 0.0068%, 0.0069%, 0.0070%, 0.0071%, 0.0072%, 0.0073%, 0.0074%, 0.0075%, 0.0076%, 0.0077%, 0.0078%, 0.0079%, 0.0080%, 0.0081%, 0.0082%, 0.0083%, 0.0084%, 0.0085%, 0.0086%, 0.0087%, 0.0088%, 0.0089%, 0.0090%, 0.0091%, 0.0092%, 0.0093%, 0.0094%, 0.0095%, 0.0096%, 0.0097%, 0.0098%, 0.0099%, 0.0100%, 0.0200%, 0.0250%, 0.0275%, 0.0300%, 0.0325%, 0.0350%, 0.0375%, 0.0400%, 0.0425%, 0.0450%, 0.0475%, 0.0500%, 0.0525%, 0.0550%, 0.0575%, 0.0600%, 0.0625%, 0.0650%, 0.0675%, 0.0700%, 0.0725%, 0.0750%, 0.0775%, 0.0800%, 0.0825%, 0.0850%, 0.0875%, 0.0900%, 0.0925%, 0.0950%, 0.0975%, 0.1000%, 0.1250%, 0.1500%, 0.1750%, 0.2000%, 0.2250%, 0.2500%, 0.2750%, 0.3000%, 0.3250%, 0.3500%, 0.3750%, 0.4000%, 0.4250%, 0.4500%, 0.4750%, 0.5000%, 0.5250%, 0.550%, 0.5750%, 0.6000%, 0.6250%, 0.6500%, 0.6750%, 0.7000%, 0.7250%, 0.7500%, 0.7750%, 0.8000%, 0.8250%, 0.8500%, 0.8750%, 0.9000%, 0.9250%, 0.9500%, 0.9750%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 60%, 65%, 70%, 75%, 80%, 85%, 90%, 95%, or 99% or more, or any range or integer derivable therein, of at least one of, any combination of, or all of the volatile hydrocarbons, film formers, ester-based solvents, sunscreen agents, gelling agents, or any additional ingredients disclosed in this specification. In non-limiting aspects, the percentage of such ingredients can be calculated by weight or volume of the total weight of the compositions. The concentrations can vary depending on the desired effect of the compositions or on the product into which the compositions are incorporated.

2. Products

In addition to foundation primers, the compositions of the present invention can be incorporated into other cosmetic products or pharmaceutical products. Non-limiting examples of such products include hand treatment products, décolleté treatment products, sunless skin tanning products, hair products (e.g., shampoos, conditioners, colorants, dyes, bleaches, straighteners, and permanent wave products), fingernail products, moisturizing creams, skin creams and lotions, softeners, day lotions, gels, ointments, foundations, night creams, lipsticks and lip balms, toners, masks, deodorants, antiperspirants, exfoliating compositions, shaving-related products (e.g., creams, "bracers" and aftershaves), pre-moistened wipes and washcloths, tanning lotions, bath products such as oils, foot care products such as powders and sprays, skin colorant and make-up products such as foundations, blushes, rouges eye shadows and lines, lip colors and mascaras, baby products (e.g., baby lotions, oils, shampoos, powders and wet wipes), and skin or facial peel products. Additionally, the cosmetic products can be formulated as leave-on or rinse-off products.

3. Additional Ingredients

Compositions of the present invention can include additional ingredients. Non-limiting examples of additional ingredients include cosmetic ingredients (both active and non-active) and pharmaceutical ingredients (both active and non-active).

a. Cosmetic Ingredients

The CTFA Handbook describes a wide variety of non-limiting cosmetic ingredients that can be used in the context of the present invention. Examples of these ingredient classes include: fragrances (artificial and natural), dyes and color ingredients (e.g., Blue 1, Blue 1 Lake, Red 40, titanium dioxide, D&C blue no. 4, D&C green no. 5, D&C orange no. 4, D&C red no. 17, D&C red no. 33, D&C violet no. 2, D&C yellow no. 10, and D&C yellow no. 11), adsorbents, emulsifiers, stabilizers, lubricants, solvents, moisturizers (including, e.g., emollients, humectants, film formers, occlusive agents, and agents that affect the natural moisturization mechanisms of the skin), water-repellants, essential oils, vitamins (e.g., A, B, C, D, E, and K), trace metals (e.g., zinc, calcium and selenium), anti-irritants (e.g., steroids and non-steroidal anti-inflammatories), botanical extracts (e.g., aloe vera, chamomile, cucumber extract, ginkgo biloba, ginseng, and rosemary), anti-microbial agents, antioxidants (e.g., BHT), chelating agents (e.g., disodium EDTA and tetrasodium EDTA), preservatives (e.g., methylparaben and propylparaben), pH adjusters (e.g., sodium hydroxide and citric acid), absorbents (e.g., aluminum starch octenylsuccinate, kaolin, corn starch, oat starch, cyclodextrin, talc, and zeolite), skin bleaching and lightening agents (e.g., hydroquinone and niacinamide lactate), humectants (e.g., propylene glycol, butylene glycol, pentylene glycol, sorbitol, urea, and manitol), exfoliants (e.g., alpha-hydroxyacids, and beta-hydroxyacids such as lactic acid, glycolic acid, and salicylic acid; and salts thereof) waterproofing agents (e.g., magnesium/aluminum hydroxide stearate), skin conditioning agents (e.g., aloe extracts, allantoin, bisabolol, ceramides, dimethicone, hyaluronic acid, and dipotassium glycyrrhizate), thickening agents (e.g., substances which that can increase the viscosity of a composition such as carboxylic acid polymers, crosslinked polyacrylate polymers, polyacrylamide polymers, polysaccharides, and gums), and silicone containing compounds (e.g., silicone oils and polyorganosiloxanes). The following provides specific non-limiting examples of some of the additional ingredients that can be used with the compositions of the present invention.

i. Additional Skin Conditioning Agents and Emollients

Non-limiting examples of skin conditioning agents and emollients that can be used with the compositions of the present invention include amino acids, chondroitin sulfate, diglycerin, erythritol, fructose, glucose, glycerol polymers, glycol, 1,2,6-hexanetriol, honey, hyaluronic acid, hydrogenated honey, hydrogenated starch hydrolysate, inositol, lactitol, maltitol, maltose, mannitol, natural moisturizing factor, PEG-15 butanediol, polyglyceryl sorbitol, salts of pyrollidone carboxylic acid, potassium PCA, propylene glycol, sodium glucuronate, sodium PCA, sorbitol, sucrose, trehalose, urea, and xylitol.

Other examples include acetylated lanolin, acetylated lanolin alcohol, acrylates/C10-30 alkyl acrylate crosspolymer, acrylates copolymer, alanine, algae extract, aloe barbadensis, aloe-barbadensis extract, aloe barbadensis gel, althea officinalis extract, aluminum starch octenylsuccinate, aluminum stearate, apricot (*prunus armeniaca*) kernel oil, arginine, arginine aspartate, arnica montana extract, ascorbic acid, ascorbyl palmitate, aspartic acid, avocado (*persea gratissima*) oil, barium sulfate, barrier sphingolipids, butyl alcohol, beeswax, behenyl alcohol, beta-sitosterol, BHT, birch (*betula alba*) bark extract, borage (*borago officinalis*) extract, 2-bromo-2-nitropropane-1,3-diol, butcherbroom (*ruscus aculeatus*) extract, butylene glycol, *calendula officinalis* extract, *calendula officinalis* oil, candelilla (*euphorbia cerifera*) wax, canola oil, caprylic/capric triglyceride, cardamon (*elettaria cardamomum*) oil, carnauba (*copernicia cerifera*) wax, carrageenan (*chondrus crispus*), carrot (*daucus carota sativa*) oil, castor (*ricinus communis*) oil, ceramides, ceresin, ceteareth-5, ceteareth-12, ceteareth-20, cetearyl octanoate, ceteth-20, ceteth-24, cetyl acetate, cetyl octanoate, cetyl palmitate, chamomile (*anthemis nobilis*) oil, cholesterol, cholesterol esters, cholesteryl hydroxystearate, citric acid, clary (*salvia sclarea*) oil, cocoa (*theobroma cacao*) butter, coco-caprylate/caprate, coconut (*cocos nucifera*) oil, collagen, collagen amino acids, corn (*zea mays*) oil, fatty acids, decyl oleate, dextrin, diazolidinyl urea, dimethicone copolyol, dimethiconol, dioctyl adipate, dioctyl succinate, dipentaerythrityl hexacaprylate/hexacaprate, DMDM hydantoin, DNA, erythritol, ethoxydiglycol, ethyl linoleate, eucalyptus globulus oil, evening primrose (*oenothera biennis*) oil, fatty acids, fructose, gelatin, geranium maculatum oil, glucosamine, glucose glutamate, glutamic acid, glycereth-26, glycerol, glyceryl distearate, glyceryl hydroxystearate, glyceryl laurate, glyceryl linoleate, glyceryl myristate, glyceryl oleate, glyceryl stearate, glyceryl stearate SE, glycine, glycol stearate, glycol stearate SE, glycosaminoglycans, grape (*vitis vinifera*) seed oil, hazel (*corylus americana*) nut oil, hazel (*corylus avellana*) nut oil, hexylene glycol, honey, hyaluronic acid, hybrid safflower (*carthamus tinctorius*) oil, hydrogenated castor oil, hydrogenated coco-glycerides, hydrogenated coconut oil, hydrogenated lanolin, hydrogenated lecithin, hydrogenated palm glyceride, hydrogenated palm kernel oil, hydrogenated soybean oil, hydrogenated tallow glyceride, hydrogenated vegetable oil, hydrolyzed collagen, hydrolyzed elastin, hydrolyzed glycosaminoglycans, hydrolyzed keratin, hydrolyzed soy protein, hydroxylated lanolin, hydroxyproline, imidazolidinyl urea, iodopropynyl butylcarbamate, isocetyl stearate, isocetyl stearoyl stearate, isodecyl oleate, isopropyl isostearate, isopropyl lanolate, isopropyl myristate, isopropyl palmitate, isopropyl stearate, isostearamide DEA, isostearic acid, isostearyl lactate, isostearyl neopentanoate, jasmine (*jasminum officinale*) oil, jojoba (*buxus chinensis*) oil, kelp, kukui (*aleurites moluccana*) nut oil, lactamide MEA, laneth-16, laneth-10 acetate, lanolin, lanolin acid, lanolin alcohol, lanolin oil, lanolin wax, lavender (*lavandula angustifolia*) oil, lecithin, lemon (*citrus medica limonum*) oil, linoleic acid, linolenic acid, macadamia ternifolia nut oil, magnesium stearate, magnesium sulfate, maltitol, matricaria (*chamomilla recutita*) oil, methyl glucose sesquistearate, methylsilanol PCA, microcrystalline wax, mineral oil, mink oil, mortierella oil, myristyl lactate, myristyl myristate, myristyl propionate, neopentyl glycol dicaprylate/dicaprate, octyldodecanol, octyldodecyl myristate, octyldodecyl stearoyl stearate, octyl hydroxystearate, octyl palmitate, octyl salicylate, octyl stearate, oleic acid, olive (*olea europaea*) oil, orange (*citrus aurantium dulcis*) oil, palm (*elaeis guineensis*) oil, palmitic acid, pantethine, panthenol, panthenyl ethyl ether, paraffin, PCA, peach (*prunus persica*) kernel oil, peanut (*arachis hypogaea*) oil, PEG-8 C12-18 ester, PEG-15 cocamine, PEG-150 distearate, PEG-60 glyceryl isostearate, PEG-5 glyceryl stearate, PEG-30 glyceryl stearate, PEG-7 hydrogenated castor oil, PEG-40 hydrogenated castor oil, PEG-60 hydrogenated castor oil, PEG-20 methyl glucose sesquistearate, PEG40 sorbitan peroleate, PEG-5 soy sterol, PEG-10 soy sterol, PEG-2 stearate, PEG-8 stearate, PEG-20 stearate, PEG-32 stearate, PEG40 stearate, PEG-50 stearate, PEG-100 stearate, PEG-150 stearate, pentadecalactone, peppermint (*mentha piperita*) oil, petrolatum, phospholipids, polyamino sugar condensate, polyglyceryl-3 diisostearate, polyquaternium-24, polysorbate 20, polysorbate 40, polysorbate 60, polysorbate 80, polysorbate 85, potassium myristate, potassium palmitate, potassium sorbate, potassium stearate, propylene glycol, propylene glycol dicaprylate/dicaprate, propylene glycol dioctanoate, propylene glycol dipelargonate, propylene glycol laurate, propylene glycol stearate, propylene glycol stearate SE, PVP, pyridoxine dipalmitate, quaternium-15, quaternium-18 hectorite, quaternium-22, retinol, retinyl palmitate, rice (*oryza sativa*) bran oil, RNA, rosemary (*rosmarinus officinalis*) oil, rose oil, safflower (*carthamus tinctorius*) oil, sage (*salvia officinalis*) oil, salicylic acid, sandalwood (*santalum album*) oil, serine, serum protein, sesame (*sesamum indicum*) oil, silk powder, sodium chondroitin sulfate, sodium hyaluronate, sodium lactate, sodium palmitate, sodium PCA, sodium polyglutamate, sodium stearate, soluble collagen, sorbic acid, sorbitan laurate, sorbitan oleate, sorbitan palmitate, sorbitan sesquioleate, sorbitan stearate, sorbitol, soybean (*glycine soja*) oil, sphingolipids, squalane, squalene, stearamide MEA-stearate, stearic acid, stearoxy dimethicone, stearoxytrimethylsilane, stearyl alcohol, stearyl glycyrrhetinate, stearyl heptanoate, stearyl stearate, sunflower (*helianthus annuus*) seed oil, sweet almond (*prunus amygdalus* dulcis) oil, synthetic beeswax, tocopheryl linoleate, tridecyl neopentanoate, tridecyl stearate, triethanolamine, tristearin, urea, vegetable oil, water, waxes, wheat (*triticum vulgare*) germ oil, and ylang ylang (*cananga odorata*) oil.

ii. Antioxidants

Non-limiting examples of antioxidants that can be used with the compositions of the present invention include acetyl cysteine, ascorbic acid polypeptide, ascorbyl dipalmitate, ascorbyl methylsilanol pectinate, ascorbyl palmitate, ascorbyl stearate, BHA, BHT, t-butyl hydroquinone, cysteine, cysteine HCl, diamylhydroquinone, di-t-butylhydroquinone, dicetyl thiodipropionate, dioleyl tocopheryl methylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isooctyl thioglycolate, kojic acid, magnesium ascorbate, magnesium ascorbyl phosphate, methylsilanol ascorbate, natural botanical anti-oxidants such as green tea or grape seed extracts, nordihydroguaiaretic acid, octyl gallate, phenylthioglycolic acid, potassium ascorbyl tocopheryl phosphate, potassium sulfite, propyl gallate, quinones, rosmarinic acid, sodium ascorbate, sodium bisulfite, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocophersolan, tocopheryl linoleate, tocopheryl nicotinate, tocopheryl succinate, and tris(nonylphenyl)phosphite.

iii. Structuring Agents

In other non-limiting aspects, the compositions of the present invention can include a structuring agent. Structuring agents, in certain aspects, assist in providing rheological characteristics to the composition to contribute to the composition's stability. In other aspects, structuring agents can also function as an emulsifier or surfactant. Non-limiting examples of structuring agents include stearic acid, palmitic acid, stearyl alcohol, cetyl alcohol, behenyl alcohol, stearic acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof.

iv. Emulsifiers

In some non-limiting aspects, the compositions can include one or more emulsifiers. Emulsifiers can reduce the interfacial tension between phases and improve the formulation and stability of an emulsion. The emulsifiers can be nonionic, cationic, anionic, and zwitterionic emulsifiers (See McCutcheon's (1986); U.S. Pat. Nos. 5,011,681; 4,421,769; 3,755,560). Non-limiting examples include esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps, TEA stearate, DEA oleth-3 phosphate, polyethylene glycol 20 sorbitan monolaurate (polysorbate 20), polyethylene glycol 5 soya sterol, steareth-2, steareth-20, steareth-21, ceteareth-20, PPG-2 methyl glucose ether distearate, ceteth-10, polysorbate 80, cetyl phosphate, potassium cetyl phosphate, diethanolamine cetyl phosphate, polysorbate 60, glyceryl stearate, PEG-100 stearate, and mixtures thereof.

v. Silicone Containing Compounds

In non-limiting aspects, silicone containing compounds include any member of a family of polymeric products whose molecular backbone is made up of alternating silicon and oxygen atoms with side groups attached to the silicon atoms. By varying the—Si—O— chain lengths, side groups, and crosslinking, silicones can be synthesized into a wide variety of materials. They can vary in consistency from liquid to gel to solids.

The silicone containing compounds that can be used in the context of the present invention include those described in this specification or those known to a person of ordinary skill in the art. Non-limiting examples include silicone oils (e.g., volatile and non-volatile oils), gels, and solids. In preferred aspects, the silicon containing compounds includes a silicone oils such as a polyorganosiloxane. Non-limiting examples of polyorganosiloxanes include dimethicone, cyclomethicone, phenyl trimethicone, trimethylsilylamodimethicone, stearoxytrimethylsilane, or mixtures of these and other organosiloxane materials in any given ratio in order to achieve the desired consistency and application characteristics depending upon the intended application (e.g., to a particular area such as the skin, hair, or eyes). A "volatile silicone oil" includes a silicone oil have a low heat of vaporization, i.e. normally less than about 50 cal per gram of silicone oil. Non-limiting examples of volatile silicone oils include: cyclomethicones such as Dow Corning 344 Fluid, Dow Corning 345 Fluid, Dow Corning 244 Fluid, and Dow Corning 245 Fluid, Volatile Silicon 7207 (Union Carbide Corp., Danbury, Conn.); low viscosity dimethicones, i.e. dimethicones having a viscosity of about 50 cst or less (e.g., dimethicones such as Dow Corning 200-0.5 cst Fluid). The Dow Corning Fluids are available from Dow Corning Corporation, Midland, Mich. Cyclomethicone and dimethicone are described in the Third Edition of the CTFA Cosmetic Ingredient Dictionary (incorporated by reference) as cyclic dimethyl polysiloxane compounds and a mixture of fully methylated linear siloxane polymers end-blocked with trimethylsiloxy units, respectively. Other non-limiting volatile silicone oils that can be used in the context of the present invention include those available from General Electric Co., Silicone Products Div., Waterford, N.Y. and SWS Silicones Div. of Stauffer Chemical Co., Adrian, Mich.

vi. Essential Oils

Essential oils include oils derived from herbs, flowers, trees, and other plants. Such oils are typically present as tiny droplets between the plant's cells, and can be extracted by several method known to those of skill in the art (e.g., steam distilled, enfleurage (i.e., extraction by using fat), maceration, solvent extraction, or mechanical pressing). When these types of oils are exposed to air they tend to evaporate (i.e., a volatile oil). As a result, many essential oils are colorless, but with age they can oxidize and become darker. Essential oils are insoluble in water and are soluble in alcohol, ether, fixed oils (vegetal), and other organic solvents. Typical physical characteristics found in essential oils include boiling points that vary from about 160° to 240° C. and densities ranging from about 0.759 to about 1.096.

Essential oils typically are named by the plant from which the oil is found. For example, rose oil or peppermint oil are derived from rose or peppermint plants, respectively. Non-limiting examples of essential oils that can be used in the context of the present invention include sesame oil, macadamia nut oil, tea tree oil, evening primrose oil, Spanish sage oil, Spanish rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, eucalyptus oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, or ylang ylang. Other essential oils known to those of skill in the art are also contemplated as being useful within the context of the present invention.

vii. Thickening Agents

Thickening agents, including thickener or gelling agents, include substances that can increase the viscosity of a composition. Thickeners include those that can increase the viscosity of a composition without substantially modifying the efficacy of the active ingredient within the composition. Thickeners can also increase the stability of the compositions of the present invention.

Non-limiting examples of additional thickening agents that can be used in the context of the present invention include carboxylic acid polymers, crosslinked polyacrylate polymers, polyacrylamide polymers, polysaccharides, and gums. Examples of carboxylic acid polymers include crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol (see U.S. Pat. Nos. 5,087,445; 4,509,949; 2,798,053). Examples of commercially available carboxylic acid polymers include carbomers, which are homopolymers of acrylic acid crosslinked with allyl ethers of sucrose or pentaerytritol (e.g., Carbopol™ 900 series from B. F. Goodrich).

Non-limiting examples of crosslinked polyacrylate polymers include cationic and nonionic polymers. Examples are described in U.S. Pat. Nos. 5,100,660; 4,849,484; 4,835,206; 4,628,078; 4,599,379).

Non-limiting examples of polyacrylamide polymers (including nonionic polyacrylamide polymers including substituted branched or unbranched polymers) include polyacrylamide, isoparaffin and laureth-7, multi-block copolymers of acrylamides and substituted acrylamides with acrylic acids and substituted acrylic acids.

Non-limiting examples of polysaccharides include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Another example is an alkyl substituted cellulose where the hydroxy groups of the cellulose polymer is hydroxyalkylated (preferably hydroxy ethylated or hydroxypropylated) to form a hydroxyalkylated cellulose which is then further modified with a $C_{10}$-$C_{30}$ straight chain or branched chain alkyl group through an ether linkage. Typically these polymers are ethers of $C_{10}$-$C_{30}$ straight or branched chain alcohols with hydroxyalkylcelluloses. Other useful polysaccharides include scleroglucans comprising a linear chain of (1-3) linked glucose units with a (1-6) linked glucose every three unit.

Non-limiting examples of gums that can be used with the present invention include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluroinic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboyxmethyl dextran, sodium carrageenan, tragacanth gum, xanthan gum, and mixtures thereof.

b. Pharmaceutical Ingredients

Pharmaceutical ingredients are also contemplated as being useful with the emulsion compositions of the present invention. Non-limiting examples of pharmaceutical ingredients include anti-acne agents, agents used to treat rosacea, analgesics, anesthetics, anorectals, antihistamines, anti-inflammatory agents including non-steroidal anti-inflammatory drugs, antibiotics, antifungals, antivirals, antimicrobials, anti-cancer actives, scabicides, pediculicides, antineoplastics, antiperspirants, antipruritics, antipsoriatic agents, antiseborrheic agents, biologically active proteins and peptides, burn treatment agents, cauterizing agents, depigmenting agents, depilatories, diaper rash treatment agents, enzymes, hair growth stimulants, hair growth retardants including DFMO and its salts and analogs, hemostatics, kerotolytics, canker sore treatment agents, cold sore treatment agents, dental and periodontal treatment agents, photosensitizing actives, skin protectant/barrier agents, steroids including hormones and corticosteroids, sunburn treatment agents, sunscreens, transdermal actives, nasal actives, vaginal actives, wart treatment agents, wound treatment agents, wound healing agents, etc.

G. Kits

Kits are also contemplated as being used in certain aspects of the present invention. For instance, a composition of the present invention can be included in a kit. A kit can include a container. Containers can include a bottle, a metal tube, a laminate tube, a plastic tube, a dispenser, a pressurized container, a barrier container, a package, a compartment, a lipstick container, a compact container, cosmetic pans that can hold cosmetic compositions, or other types of containers such as injection or blow-molded plastic containers into which the dispersions or compositions or desired bottles, dispensers, or packages are retained. The kit and/or container can include indicia on its surface. The indicia, for example, can be a word, a phrase, an abbreviation, a picture, or a symbol.

The containers can dispense a pre-determined amount of a composition. In other embodiments, the container can be squeezed (e.g., metal, laminate, or plastic tube) to dispense a desired amount of the composition. The composition can be dispensed as a spray, foam, an aerosol, a liquid, a fluid, or a semi-solid. The containers can have spray, pump, or squeeze mechanisms. A kit can also include instructions for using the kit and/or compositions. Instructions can include an explanation of how to apply, use, and maintain the compositions.

EXAMPLES

The following examples are included to demonstrate certain non-limiting aspects of the invention. It should be appreciated by those of skill in the art that the techniques disclosed in the examples which follow represent techniques discovered by the inventor to function well in the practice of the invention. However, those of skill in the art should, in light of the present disclosure, appreciate that many changes can be made in the specific embodiments which are disclosed and still obtain a like or similar result without departing from the spirit and scope of the invention.

Example 1

Non-Limiting Composition

Table 1 described a non-limiting foundation primer gel in the context of the compositions of the present invention. The gel has a translucent appearance upon visual inspection.

TABLE 1

| Ingredients** | % Concentration (by weight) |
| --- | --- |
| Isododecane | q.s. (at least 50%) |
| Homosalate | 9 |
| Dimethicone/Bis-Isobutyle PPG-20 Crosspolymer | 5.55 |
| Octisalate | 5 |
| Polysilicone-11 | 3.72 |
| VP/Hexadecene Copolymer | 3.5 |
| Octocrylene | 3 |
| Avobenzone | 2.5 |
| Silica | 2.5 |
| C12-15 Alkyl Benzoate | 2.1 |
| Polyester-7 | 1.5 |
| Tribehenin | 1 |
| Neopentyl Glycol Diheptanoate | 1 |
| Dipropylene Glycol Dibenzoate | 0.75 |
| PPG-15 Stearyl Ether Benzoate | 0.15 |
| TOTAL | 100 |

The composition described in Table 1 was prepared as follows: (1) Add Homosalate, Octisalate, Octocrylene, C12-15 Alkyl Benzoate, Dipropylene Glycol Dibenzoate, PPG-15 Stearyl Ether Benzoate, Polyester-7, Neopentyl Glycol Diheptanoate, PVP/Hexadecene Copolymer, and Avobenzone to mixing vessel, then mix at 70-75° C. with Propeller mixer until uniform; (2) add Glyceryl Tribehenate and maintain mixing temperatures and mixing speed until batch uniform and transparent; (3) increase Propeller mixing to high speed, then add Isododecane, Polysilicone-11, Isododecane, and Dimethicone/Bis-Isobutyl PPG-20 Crosspolymer, and let batch cool to 45-55° C., mixing until gels are completely dispersed; and (4) add Silica into batch with high speed Propeller mixing and allow batch to cool between 38 to 45° C., and continue mixing until powder is completely dispersed, and batch appears uniform.

The gel dries within about 30 seconds to 1-2 minutes after being topically applied to skin. Drying is confirmed by comparing the flowability of the composition immediately after topical application to skin, in which the composition is still in a flowable state, to the composition 30 seconds, 1 minute, and 2 minutes after topical application to skin, in which the composition is no longer in a flowable state.

Example 2

SPF Protection Data

The gel described in Table 1 was tested (referred to as "Table 1 Gel") to determine the static sun protection factor (SPF) as a sunscreen according to the FDA Proposed Amendment of Final Monograph 2007.

Materials and Methods: Assays were conducted according to the procedures and criteria outlined in the Food and Drug Administration (FDA) proposed Amendment of Final Monograph of 2007 for sunscreen testing published in the Federal Register, vol. 72, No. 165, Aug. 27, 2007. The subject selection criteria included:

1. According to the FDA criteria, only subjects with Skin Types I, II, or III were selected:
   Type I: Always burns easily; never tans (sensitive);
   Type II: Always burns easily; tans minimally (sensitive); and
   Type III: Burns moderately; tans gradually (light brown) (normal)
2. At least 18 years old, providing legally effective, written informed consent.
3. No dermatological or other medical or physical condition which would interfere with the test results and might be confused for a skin reaction.
4. No history of abnormal response to sunlight or be taking medication that might produce an abnormal response to sunlight.
5. Not currently suntanned or sun burnt.
6. Not pregnant or nursing.
7. Willing to avoid sun and tanning lamp exposure during the study.

On the first day of the study each subject received a series of UV doses from a Xenon arc solar simulator to an unprotected site on the mid-back. The solar simulator was a single-port xenon arc lamp with a 1 mm WG320 UVC blocking filter, a 1 mm UG-11 visible and infrared blocking filter and a heat rejecting dichroic mirror (Model 16S, Solar light Co., PA, USA). On the second day the minimal erythema dose (MED) was determined as the lowest UV dose which produced perceptible, unambiguous erythema with clearly defined borders. 100 mg of the Table 1 Gel and 100 mg of the P2 standard sunscreen (Cosmotech laboratories, Inc. NJ) were applied to separate, adjacent 50 cm² areas of the mid-back. Each sunscreen-protected site was divided into five sub-site test areas that were at least 1 cm² in area for UV exposures. After a 15-minute drying period, UV doses ranging from 0.76 to 1.32 times the product of the MED and the expected SPF were administered to each test sunscreen-protected area. UV doses ranging from 0.76 to 1.32 times the product of the MED and 15 were administered to the standard sunscreen-protected area. A series of UV doses, ranging from 0.64 to 1.56 times the original MED, were also administered to unprotected site. On the third day, the MED was determined for the sunscreen-protected sites and the unprotected site.

The grading scale for Erythema responses to UV doses administered to untreated sites and sunscreen treated sites were:
   0 No erythemal response
   1 Minimally perceptible erythema
   2 Mild erythema with clearly defined borders (MED reaction)
   3 Moderate erythema with sharp borders
   4 Dark red erythema with sharp borders
   5 Dark red erythema with sharp borders and possible edema
   6 Intense erythema with sharp borders and edema The SPF for each formula on each panelist was calculated using the following formula:

$$SPF = \frac{MED \text{ Test Material or Standard}}{MED \text{ Unprotected Control}}$$

The Mean SPF Value for the panel was calculated as the arithmetic average of all the individual values.

The label claim SPF was calculated as follows: (Mean SPF Value−A) rounded down to the nearest whole number, where $A = ts/\sqrt{n}$, t=Upper 5% of student's t distribution, s=standard deviation, n=number of subjects.

A Product Category Description (PCD) was assigned based on the following:
(i) If 50+A<Mean SPF, the PCD is "Highest";
(ii) If 30+A</=Mean SPF</=50+A, PCD is "High";
(iii) If 15+A</=Mean SPF<30+A, PCD is "Medium";
(iv) If 2+A<1=Mean SPF<15+A, PCD is "Low"; and
(v) If Mean SPF<2+A, the product shall not be labeled as an OTC sunscreen drug product and may not display an SPF value.

Results: Twenty subjects (ages 19 to 63 years) completed the study. The mean static SPF of the Table 1 Gel was 16.2 (n=20, SD=1.8). The mean SPF-A, rounded down to the nearest whole number was 15. The mean static SPF of the P2 standard was 16.7 (n=20, SD=1.7). The mean static SPF of the P2 standard was within the required range. No adverse events were reported.

Conclusion: The mean static SPF for the gel described in Table 1 of this specification was 16.2. Therefore, it meets the labeling requirement for static SPF 15 and PCD of "Medium" according to the FDA Monograph.

Example 3

UVA Protection Data

The gel described in Table 1 was tested (referred to as "Table 1 Gel") to evaluate its UVA protection efficacy using the in vitro Critical Wavelength determination method of Diffey. (Diffey BL. A method for broad-spectrum classification of sunscreens—Int. J. Cosmet. Sci. 1994; 16:47-52.).

Materials and Methods: The UV transmission spectrum was measured for a 5 cm×5 cm roughened Polymethyl Methacrylate plate (PMMA) Substrate, and the Table 1 Gel was applied to the substrate at approximately 1 mg/cm². UV transmission spectrum of the Table 1 Gel was determined using an Optronic Laboratories Spectroradiometer, Model 754, and the UV absorbance was calculated for each wavelength ($\lambda$). The critical wavelength ($\lambda c$) was determined as the wavelength at which the integral of the spectral absorbance curve reaches 90 percent of the integral from 290 nm to 400 nm according to the method of Diffey where critical wavelengthis defined as the wavelength below which 90% of the area under the curve ($A_\lambda$) resides.

A series of absorbance values were calculated for each of the five separate plates to which the Table 1 Gel had been applied. The absorbance at each wavelength increment ($A_\lambda$) was calculated:

$$A_\lambda = \log(C_\lambda / P_\lambda)$$

where $$C_\lambda = \sqrt[n]{(c_\lambda[1] \times c_\lambda[2] \times \ldots \times c_\lambda[n])}$$

$$P_\lambda = \sqrt[n]{(p_\lambda[1] \times p_\lambda[2] \times \ldots \times p_\lambda[n])}$$

$c_\lambda$=the arithmetic mean of transmission measurements taken at the measurement point n and at wavelength $\lambda$ for the reference sample (glycerine-treated roughened PMMA plate);

$p_\lambda$=the arithmetic mean of transmission measurements taken at the measurement point n and at wavelength for the irradiated sunscreen product treated sample (roughened PMMA plate).

The Critical Wavelength is calculated for each irradiated plate as follows:

$$\int_{290}^{\lambda c} A\lambda \cdot d\lambda = 0.9 \int_{290}^{400} A\lambda \cdot d\lambda$$

The final Critical Wavelength value for the Table 1 Gel is the mean of the values recorded for each measured, irradiated, product-treated plate.

Results: The Table 1 Gel had a critical wavelength value of 376 nm and satisfied the criterion for "Broad Spectrum" labeling according to the method outlined above.

Conclusion: The results of this assay support the 'Broad Spectrum' claim for the gel identified in Table 1.

Example 4

Protection Grade of UVA Data

The gel described in Table 1 was tested (referred to as "Table 1 Gel") to evaluate its Protection Grade of UVA ("PFA") using persistent pigment darkening (PPD) as a visual endpoint.

Materials and Methods: The assay was conducted according to the procedures and criteria outlined in the Japan Cosmetic Industry Association (JCIA) Expert Committee on Ultra-Violet Standard Protection Factor of UVA (PFA) Test Method (Nov. 15, 1996) pp 50-59. The subject selection criteria was the same as that described above in Example 2.

Persistent Pigment-Darkening was determined for each subject prior to the testing to determine the Minimal Persistent Pigment Darkening (MPPD) dose. The subject's MPPD is the time interval or dosage of UVA light exposure sufficient to produce defined darkening (grade 1.0 below) on designated test sites.

The Xenon Arc Solar Simulator (Solar Light Company, Philadelphia, Pa.) filtered so that it provided a continuous emission spectrum covering the UVA range (320 to 400 nm) by using a Schott WG 335/3 mm and UG 11/1 mm filters was used as the light source.

The gel described in Table 1 and a control material (per the JCIA, provided by SRL) were applied on the backs of the subjects to obtain 2 mg/cm$^2$. The test sites (protected and unprotected) were exposed to UVA light no less than 15 minutes after the application of the Table 1 gel and control materials. The UVA doses for the PFA determination were based on the MPPD dose for the panelist (unprotected skin) and the expected PFA for the Table 1 and control sunscreens. Five UVA doses that were applied to each area were fractions of the expected value according to the Table 2 below:

TABLE 2

| Multiple of Subject MPPD and Expected PFA | | | | |
|---|---|---|---|---|
| 0.64 | 0.08 | 1.00 | 1.25 | 1.56 |

All test sites were evaluated within 2 to 4 hours post-irradiation to determine Minimal Persistent Pigment Darkening as defined below. The Response Evaluation Scale included the following:

0 Negative, no visible pigment darkening
0.5 Minimal pigment darkening
1.0 Defined pigment darkening (MPPD)
2.0 Moderate pigment darkening
3.0 Marked pigment darkening The PFA was calculated using the following formula:

$$PFA = \frac{MPPD \text{ Protected Skin (Test Material or Standard)}}{MPPD \text{ Unprotected Skin}}$$

For labeling purposes, a sunscreen product may be categorized as follows:

| PFA Value | PA Value |
|---|---|
| Over 2, less than 4 | PA+ |
| 4 or more, less than 8 | PA++ |
| 8 or more | PA+++ |

Results: Ten subjects were used and all completed the study. No adverse reactions were observed in any of the subjects. The mean PFA values for the Table 1 and control materials are presented below:

| Test Material | PFA (Mean ± Standard Deviation | Standard Error (% of the mean) |
|---|---|---|
| Table 1 Gel | 8.7 ± 1.5 | 5.5% |
| PFA Control (JCIA Standard) | 4.2 ± 0.60 | 4.6% |

The standard errors (as a percentage of the mean PFA) for both the Table 1 Gel and the PFA Control were within acceptable limits (<10%) and the PFA for the PFA Control was within the range of 3.75±1.01 (2.74 to 4.76) and therefore the assay was considered valid.

Conclusion: The results of this assay support the UVA protection claim (PFA and PA rating) for the Table 1 Gel. Therefore, the Gel can be categorized as a PA+++ protective sunscreen product.

Example 5

Stability Data

Table 2 provides stability data for the gel described in Table 1.

TABLE 3

| Test Conditions | Time Interval | Test Result* |
|---|---|---|
| 5° C. | 0 Days | No white particles upon visual |
| 5° C. | 3 Days | No white particles upon visual |
| 5° C. | 7 Days | No white particles upon visual |
| 5° C. | 10 Days | No white particles upon visual |
| 5° C. | 4 Weeks | No white particles upon visual |
| Freeze/Thaw −10° C./25° C. | 0 Days | No white particles upon visual |
| Freeze/Thaw −10° C./25° C. | 6 Days | No white particles upon visual |
| Freezer −10° C. | 0 Days | No white particles upon visual |
| Freezer −10° C. | 24 Hours | No white particles upon visual |
| Freezer −10° C. | 3 Days | No white particles upon visual |
| Freezer −10° C. | 7 Days | No white particles upon visual |
| Freezer −10° C. | 10 Days | No white particles upon visual |
| Freezer −10° C. | 4 Weeks | Numerous white particles observed. After 3 days at room temperature (~20-25° C.), white particles disappeared. |

*"No white particles" means that all of the ingredients within the Table 1 Gel remained solubilized.

Example 6

In Vivo Data

The information in Table 4 provides in vivo data concerning the aesthetic/tactile properties of using the gel described in Table 1. Scoring was based on a scale of 1-5 as follows: 1=Strongly Disagree; 2=Somewhat Disagree; 3=Neither Agree Nor Disagree; 4=Somewhat Agree; 5=Strongly Agree.

TABLE 4

| Question | # of Panelists | Average Score |
| --- | --- | --- |
| Applies Evenly | 58 | 4.7 |
| Does not feel oily or greasy | 58 | 4.5 |
| Is suitable for my skin type | 57 | 4.5 |
| Is lightweight | 57 | 4.6 |
| Absorbs quickly | 58 | 4.6 |
| Dries quickly | 58 | 4.5 |
| Applies smoothly | 58 | 4.7 |
| Refines skin texture | 58 | 3.9 |
| Helps to reduce the appearance of pores | 56 | 3.7 |
| Provides a matte finish | 58 | 4.3 |
| Visibly minimizes the appearance of wrinkles | 55 | 3.2 |
| Helps even my skin tone | 58 | 3.6 |
| Allows my foundation to be easily applied | 58 | 4.4 |
| Provides a natural finish | 57 | 4.2 |
| Provides a smooth canvas for foundation application | 57 | 4.4 |
| Helps perfect my complexion | 58 | 3.8 |
| Provides a translucent finish | 56 | 4.2 |
| Visibly minimizes the appearance of fine lines | 55 | 3.3 |
| Provides a flawless finish | 56 | 4.0 |
| Perfects my skin | 57 | 3.6 |
| Helps skin look smoother | 58 | 4.1 |
| Primer feels luxurious | 58 | 4.2 |
| Does not leave an oily or greasy after feel | 58 | 4.6 |
| Improves the application of the foundation | 58 | 4.3 |
| Extends the wear of my makeup | 57 | 4.0 |
| Helps my foundation remain fresh | 57 | 4.0 |
| Helps prevent oil breakthrough | 51 | 3.8 |
| Skin looks younger | 55 | 3.5 |
| Helps foundation go on smoother | 57 | 4.2 |
| Provides luxurious after feel | 56 | 4.1 |
| Skin looks healthier | 56 | 3.5 |
| Provides a shine free canvas | 55 | 4.1 |
| Helps skin look firmer | 54 | 3.3 |
| Helps to reduce the appearance of skin imperfections | 56 | 3.5 |

The panelists for the data in Table 4 were women aged 21 to 65. 7% of the panelists had self-classified dry skin. 32% of the panelists had self-classified normal skin with some dryness. 11% of the panelists had self-classified normal skin. 45% of the panelists had self-classified combination oil T-zone skin. 5% of the panelists had self-classified oily skin. 14% of the panelists used a cream-based foundation with the study. 47% of the panelists used a liquid-based foundation with the study. 7% of the panelists used a cream to powder-based foundation with the study. 32% of the panelists used a powder/mineral powder-based foundation with the study.

\* \* \*

All of the compositions and methods disclosed and claimed in this specification can be made and executed without undue experimentation in light of the present disclosure. While the compositions and methods of this invention have been described in terms of particular embodiments, it will be apparent to those of skill in the art that variations may be applied to the compositions and methods and in the steps or in the sequence of steps of the method described herein without departing from the concept, spirit and scope of the invention.

REFERENCES

The following references, to the extent that they provide exemplary procedural or other details supplementary to those set forth herein, are specifically incorporated herein by reference.

CTFA International Cosmetic Ingredient Dictionary and Handbook, 12$^{th}$ Ed., 2008.

The invention claimed is:

1. A topical gel composition consisting of:
   (a) at least 50% w/w isododecane;
   (b) homosalate;
   (c) dimethicone/bis-isobutyl PPG-20 crosspolymer;
   (d) octisalate;
   (e) polysilicone-11;
   (f) VP/hexadecene copolymer;
   (g) octocrylene;
   (h) avobenzone;
   (i) silica;
   (j) C12-15 alkyl benzoate;
   (k) polyester-7;
   (l) tribehenin;
   (m) neopentyl glycol diheptanoate;
   (n) dipropylene glycol dibenzoate; and
   (o) PPG-15 stearyl ether benzoate.

2. The topical gel composition of claim 1 consisting of:
   (a) 58.73% w/w isododecane;
   (b) 9% w/w homosalate;
   (c) 5.55% w/w dimethicone/bis-isobutyl PPG-20 crosspolymer;
   (d) 5% w/w octisalate;
   (e) 3.72% w/w polysilicone-11;
   (f) 3.5% w/w VP/hexadecene copolymer;
   (g) 3% w/w octocrylene;
   (h) 2.5% w/w avobenzone;
   (i) 2.5% w/w silica;
   (j) 2.1% w/w C12-15 alkyl benzoate;
   (k) 1.5% w/w polyester-7;
   (l) 1% w/w tribehenin;
   (m) 1% w/w neopentyl glycol diheptanoate;
   (n) 0.75% w/w dipropylene glycol dibenzoate; and
   (o) 0.15% w/w PPG-15 stearyl ether benzoate.

\* \* \* \* \*